United States Patent [19]

Bienayme et al.

[11] Patent Number: 5,663,459
[45] Date of Patent: Sep. 2, 1997

[54] INTERMEDIATES FOR THE PREPARATION OF VITAMIN A AND CAROTENOIDS AND PROCESS FOR THEIR PREPARATION

[75] Inventors: Hugues Bienayme, Lyons; Pierre Meilland, Chaponost, both of France

[73] Assignee: Rhone-Poulenc Nutrition Animale, Antony, France

[21] Appl. No.: 473,226

[22] Filed: Jun. 7, 1995

Related U.S. Application Data

[62] Division of Ser. No. 320,185, Oct. 7, 1994, Pat. No. 5,567,852.

[30] Foreign Application Priority Data

Oct. 7, 1993 [FR] France .................. 93 11944

[51] Int. Cl.$^6$ .................................................. C07C 33/14
[52] U.S. Cl. ..................... 568/826; 568/668; 560/259
[58] Field of Search ......................... 568/826, 608; 560/259

[56] References Cited

U.S. PATENT DOCUMENTS

| | | | |
|---|---|---|---|
| 3,057,913 | 10/1962 | Guax et al. | 568/668 |
| 3,225,102 | 12/1965 | Thompson | 568/826 |
| 3,247,239 | 4/1966 | Truscheit et al. | 568/668 |
| 3,632,860 | 1/1972 | Marbet | 568/826 |
| 3,949,006 | 4/1976 | Orashnik | 568/668 |

FOREIGN PATENT DOCUMENTS

| | | |
|---|---|---|
| 1313362 | 11/1962 | France . |
| 373 373 | 1/1964 | Switzerland . |

*Primary Examiner*—James H. Reamer
*Attorney, Agent, or Firm*—Finnegan, Henderson, Farabow, Garett & Dunner, L.L.P.

[57] ABSTRACT

The present invention relates to novel intermediates for the preparation of vitamin A and carotenoids corresponding to the formula (II):

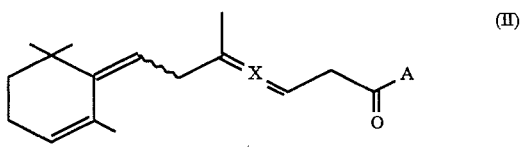

in which A represents a hydrogen or an alkyl, alkenyl or alkoxy group containing 1 to 4 carbon atoms, and X represents a carbon atom, and to a process for their preparation and their use, and further relates to compounds for preparing intermediates of formula (II) corresponding to the formula (III):

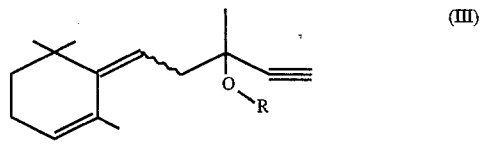

in which R represents a hydrogen atom, an alkyl group having 1 to 10 carbon atoms, an alkenyl group having 2 to 10 carbon atoms, an alkylcarbonyl, alkenylcarbonyl, alkoxyalkyl or alkoxyalkenyl group in which the alkyl groups have 1 to 10 carbon atoms and the alkenyl groups have 2 to 10 carbon atoms, each of said groups being linear or branched and each being substituted or unsubstituted.

2 Claims, No Drawings

INTERMEDIATES FOR THE PREPARATION OF VITAMIN A AND CAROTENOIDS AND PROCESS FOR THEIR PREPARATION

This is a division of application Ser. No. 08/320,185, filed Oct. 7, 1994 now U.S. Pat. No. 5,567,852.

The present invention relates to novel intermediates of vitamin A and carotenoids. It relates more particularly to allenic ketones and to the preparation of intermediates thereof and the process for their production.

The disclosure of U.S. patent application Ser. No. 08/320,150, filed Oct. 7, 1994, now U.S. Pat. No. 5,563,297, entitled "Intermediates for the Preparation of Vitamin A and Carotenoids and Process for their Preparation," and naming Hugues Bienayme as the inventor, is specifically incorporated by reference herein.

It is known according to the article by G. Saucy and R. Marbet published in Helvetica Chemica Acta, Vol. 50, pages 1158–1167 (1967), to perform a Claisen reaction on a propargyl alcohol in order to create the following terpenic linkages:

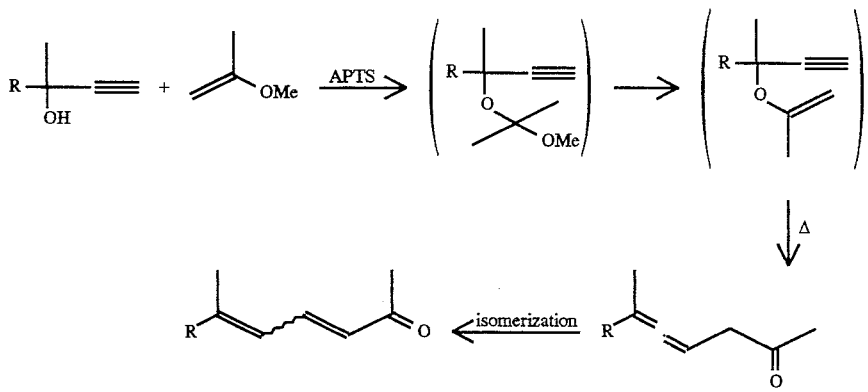

However, when the alcohol is both propargylic and allylic, that is to say when R represents a vinylic residue, the Claisen rearrangement preferably occurs on the allylic side and with a mediocre yield, as demonstrated in the publication from Zakarova, Micropol'skya Yurkina, Filippova Kustanovich and Samokhualov published in Zj. Org. Khim. 7, 1137 (1971).

Thus, when 3-methylpenten-4-yn-3-ol and 2-methoxypropene are placed in the presence of an acid, the corresponding acetal is obtained, according to:

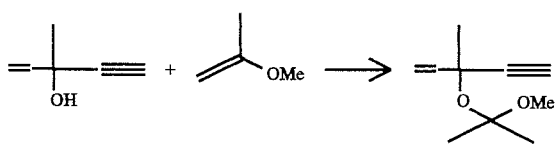

which, upon heating in the presence of paratoluenesulphonic acid, gives a low yield (30%) of a mixture of the following two ketones in a V/VI weight ratio of 6/1:

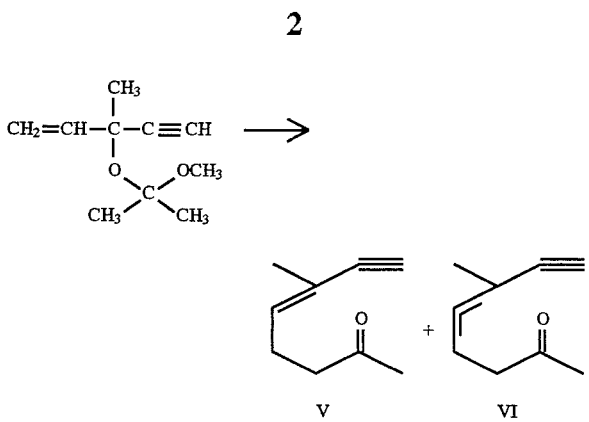

The ketone VI is very unstable and is rapidly converted by isomerism into a triene ketone in which all the double bonds are conjugated. This ketone is thus obtained with an approximate yield of 4%.

It is thus clear that it is not possible to use ethynyl-β-ionol as a starting material in order to prepare various terpenic intermediates, such as the $C_{18}$ ketone, by the Claisen rearrangement.

The present invention has made it possible to prepare allenic ketones which may be used directly in the synthesis of vitamin A or carotenoids with improved yield and selectivity relative to this publication.

The present invention relates to intermediates of vitamin A and carotenoids which correspond to formula (II):

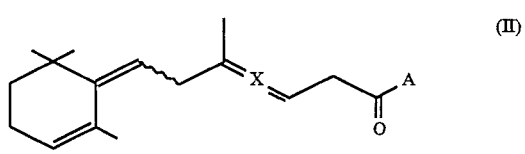

in which A represents hydrogen, an alkyl, alkenyl or alkoxy group (unit), each containing 1 to 4 carbon atoms and in which X represents a carbon atom.

The intermediate of formula (II) may be obtained by heat treatment of a compound of formula (III):

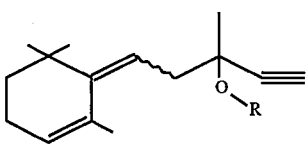
(III)

in which R represents an alkenyl, alkylcarbonyl, alkoxyalkyl or alkoxyalkenyl group, each containing 2 to 15 carbon atoms. All of these groups can be linear or branched. As is understood by one skilled in the art, these groups can be branched only if they contain more than two carbon atoms.

Among the alkenyl groups, the following units may be mentioned:

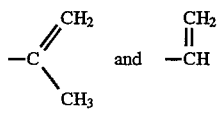

Among the alylcarbonyl groups, the following units may be mentioned:

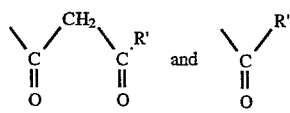

wherein R' represents an alkyl group containing 1 to 4 carbon atoms.

Among the alkoxyalkyl and alkoxyalkenyl groups, the following groups may be mentioned:

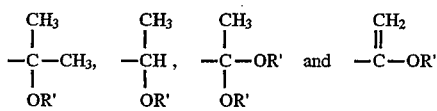

wherein R' represents an alkyl group containing 1 to 4 carbon atoms or the group:

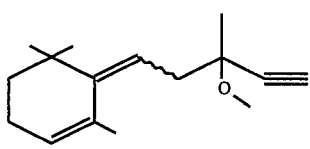

The intermediate of formula (II) may also be obtained directly by condensation of ethynyl-retro-α-ionol (III, R=H) with a 2-alkoxypropene, preferably methoxypropene, ethyl vinyl ether, vinyl acetate, an alkyl acetoacetate, diketene or an alkyl orthoacetate in the presence of an acid, by heating, preferably to between 50° C. and 200° C.

The present invention further relates to intermediates of formula (III):

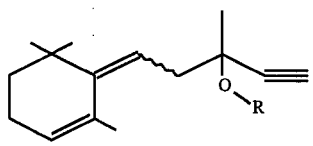
(III)

in which R represents A hydrogen atom, an alkyl group having 1 to 10 carbon atoms, an alkenyl group having 2 to 10 carbon atoms, an alkylcarbonyl, alkenylcarbonyl, alkoxyalkyl or alkoxyalkenyl group in which the alkyl groups have 1 to 10 carbon atoms and the alkenyl groups have 2 to 10 carbon atoms, all of these groups being linear or branched and being optionally substituted.

As defined herein, alkyl, alkenyl, alkoxy, alkylcarbonyl, alkenylcarbonyl, alkoxyalkyl or alkoxyalkenyl groups can be substituted or unsubstituted.

The intermediates of formula (III) wherein R is other than H can be prepared by condensation of ethynyl-retro-α-ionol with an enol ether or with an acetal containing 3 to 10 carbon atoms or an alkyl acetoacetate containing 4 to 10 carbon atoms or a trialkyl orthoacetate containing 5 to 10 carbon atoms, or diketene, all of which groups can be optionally substituted, optionally in the presence of an acid catalyst.

Ethynyl-retro-α-ionol (R=H) can be prepared by a process which consists in isomerizing β-ionone into retro-α-ionone and then in performing an ethynylation.

The conversion of β-ionone into retro-α-ionone has been described by Van Wageningen, Van der Wielen and H. Cerfontain in Synthesis Communications, 4(6), pages 325–330 (1974). It consists in placing β-ionone together with an alkoxide in a polar aprotic solvent.

The second step, ethynylation, consists in reacting acetylene with retro-α-ionone in the presence of a base chosen from organomagnesium reagents, sodium hydroxide, potassium hydroxide and alkali metal or alkaline-earth metal alkoxides. This base is preferably isobutylmagnesium chloride. The two cis and trans isomers of ethynyl-retro-α-ionol are obtained.

The compounds of formula (II) may subsequently be isomerized into the conjugated aldehyde, ketone and ester, which are intermediates in the preparation of vitamin A and carotenoids.

The present invention will be more fully described with the aid of the examples which follow, which should not be considered as limiting the invention. Please note there is no Example 3.

EXAMPLE 1

Preparation of retro-α-ionone

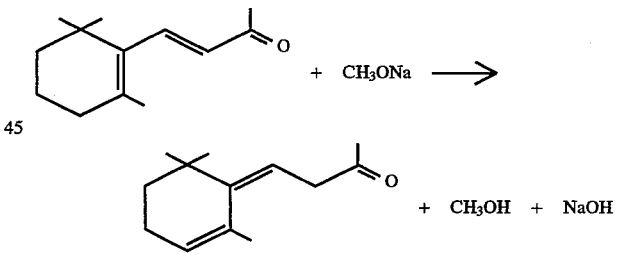

A 100 ml three-necked flask fitted with a cooling system and a submerging tube was used, with magnetic stirring.

10.0 g (50.44 mmol) of 97% pure β-ionone was placed in 45 ml of dimethyl sulphoxide. The mixture was cooled to approximately 150° C. and 3.837 g of sodium methoxide ($63.9 \times 10^{-3}$ mol) was then added with removal of the cooling bath. The duration of the addition was 23 min. A very thick red liquid was obtained. The mixture was stirred for a further 50 minutes at a temperature between 15° C. and 20° C.

The reaction mass was poured onto 150 g of water containing ice. The mixture was extracted with ether and washed with water until neutral. It was dried over magnesium sulphate.

9.96 g of product was obtained which, on distillation, gave 7.4 g distilling at 110° C. and had a purity of 94%. The yield was 71.2%.

NMR and infrared analyses showed the presence of 5% of residual β-ionone and the following two isomers:

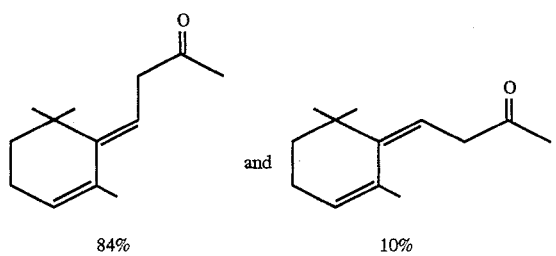

84%  10%

EXAMPLE 2

Preparation of ethynyl-retro-α-ionol (compound of formula III where R=H)

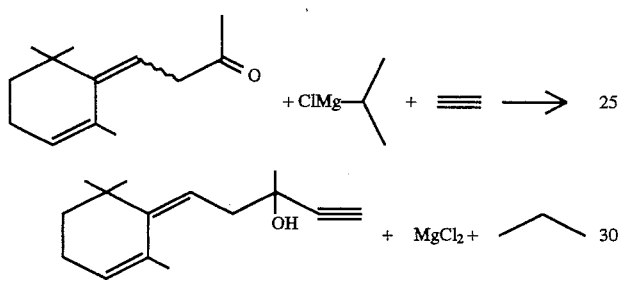

40 ml of THF was introduced at 8°–10° C. into a 250 ml three-necked reactor fitted with magnetic stirring, a condenser, a gas inlet and a dropping funnel. Acetylene was subsequently introduced continuously at a flow rate of 100 ml/min to the point of saturation.

2.31 g of isopropylmagnesium chloride was added over 25 minutes, and the temperature was maintained between 7° C. and 12° C. The solution became heterogeneous. The addition of acetylene was continued for 3 hours.

The system was flushed with nitrogen.

The compound of the preceding test (Example 1) was run in with 10 ml of THF over 8 minutes. The solution became clear. The mixture was left to react for 1 h 30 between 10° C. and 20° C. The solution obtained was hydrolysed with 0.2N HCl (20 ml) at about 4° C. to 6° C. The resulting mixture was taken up in ether, the magnesium chloride was separated out by decantation and the mixture was washed several times with ether and then with water until neutral. It was dried over magnesium sulphate.

5.34 g of crude product was obtained, which product was purified on a column of silica with a pentane/ethyl ether eluent. $15.9 \times 10^{-3}$ mol of expected product (3.47 g) and $2.48 \times 10^{-3}$ mol of retro-α-ionone (0.475 g) was obtained. The yield was approximately 67%.

NMR, infrared and mass analyses confirmed the structure of the expected product:

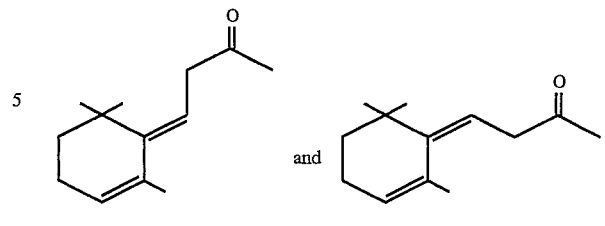

84%  10%

EXAMPLE 4

Preparation of 1,1,5-trimethyl-4-cyclohexene-9-methylhexene-6,9,10-triene methyl ketone (compound of structure II; A=CH$_3$; X=a carbon atom)

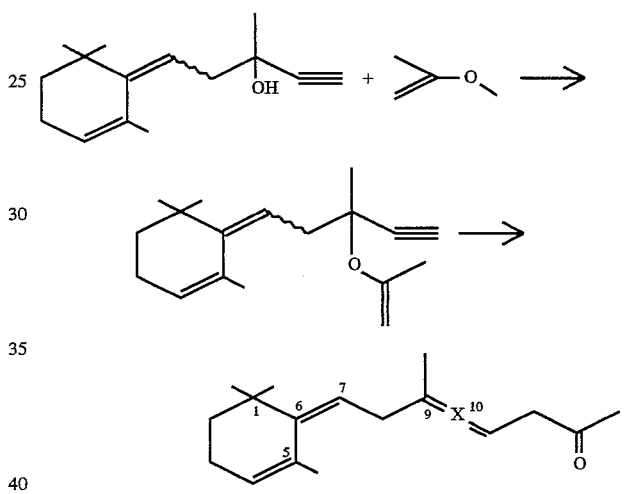

1.494 g of the product obtained in Example 2 ($6.6 \times 10^{-3}$ mol) and 2 crystals of hydroquinone were introduced into a 10 ml three-necked round-bottomed flask fitted with magnetic stirring and a condenser, followed by addition of 2.4 ml of methoxypropene ($24.3 \times 10^{-3}$ mol) and 2 grains of para-toluenesulphonic acid. The mixture was heated for 2 hours at 60° C. and then at reflux with a bath at 80° C. for 4 hours. The extent of conversion of the ethynyl-retro-β-ionol did not change any further.

The reaction medium was taken up in ether, washed with water then with sodium hydrogen carbonate solution and then again with water until neutral. The resulting solution was dried over magnesium sulphate. 1.8 g of a reaction mass was obtained, which mass was separated on a column of silica and allowed to separate into 1.27 g ($4.92 \times 10^{-3}$ mol) of the desired product (yield of 75% with respect to ethynyl-retro-α-ionol).

The NMR, infrared and mass analyses made it possible to reveal the presence of the following two isomers:

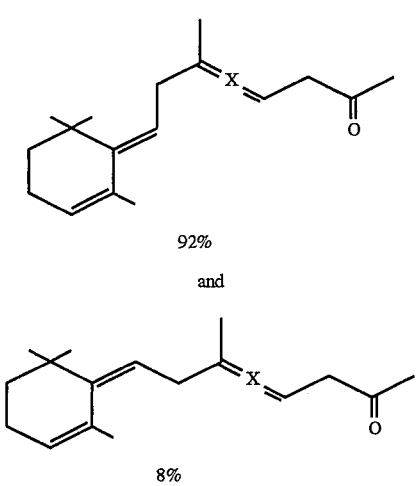

92% and

8% in which X is a carbon atom.

COMPARATIVE EXAMPLE 5

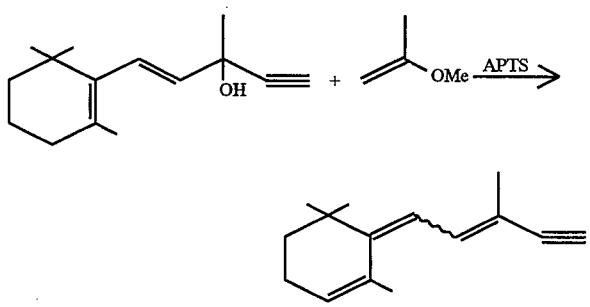

By following the experimental procedure identical to that of Example 4, but using ethynyl-β-ionol, only the dehydration product was recovered, with a yield of 67%.

COMPARATIVE EXAMPLE 6

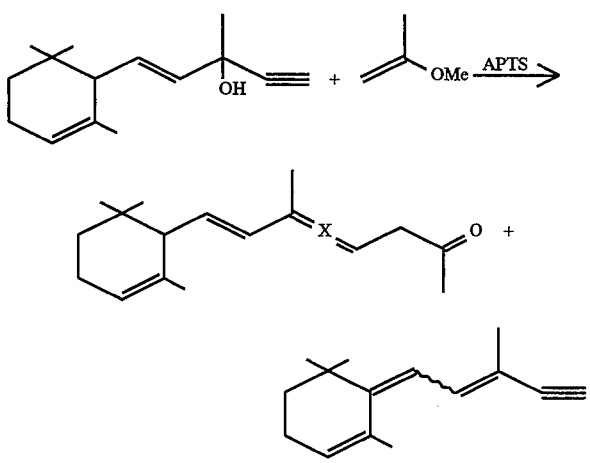

By following the experimental procedure of Example 4, but using ethynyl-α-ionol, the following was discovered:
the expected allenic ketone with a yield of 8.5%
the dehydration product with a yield of 16.5%
The extent of conversion was only 49%.

EXAMPLE 7

Rearrangement of the $C_{18}$ ketone obtained in Example 4 (II, A=$CH_3$, X=a carbon atom)

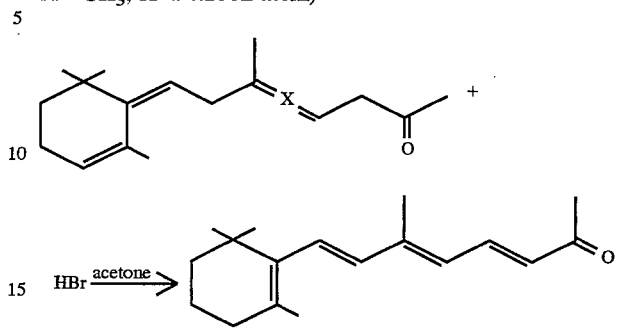

256.6 mg ($0.993 \times 10^{-3}$ mol) of the $C_{18}$ ketone obtained in Example 4 in 3 ml of acetone was introduced, under argon and at a temperature between 0° C. and 5° C., into a round-bottomed flask.

A solution of hydrobromic acid in acetone (0.854M) was prepared.

The flask was cooled in an ice-water bath and the hydrobromic acid solution (3×50 μl) was introduced over 3 hours. An extent of conversion which goes to completion was obtained in 3 hours 45 minutes.

The solution was taken up in ether and washed with water and with cold sodium hydrogen carbonate. It was dried over magnesium sulphate.

A separation was performed on silica with a pentane/$Et_2O$ (85/15) eluent. Two elution products were obtained:

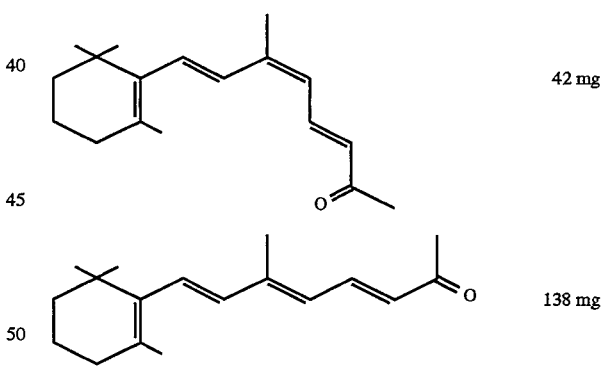

42 mg 138 mg

The yield was 70%.

EXAMPLE 8

Rearrangement of the $C_{18}$ ketone (formula II with A=$CH_3$, X=a carbon atom) into the deconjugated $C_{18}$ ketone

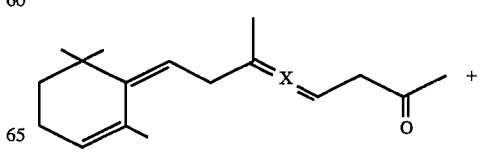

9

-continued

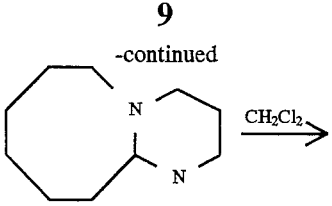

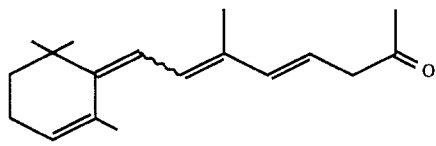

167.2 mg (0.61×10⁻³ mol) of the product obtained in Example 4 dissolved in 1 ml of methylene chloride, was introduced into a round-bottomed flask.

11 mg of diazabicycloundecene was added. The reaction was complete in 1 hour 45 minutes.

The reaction medium was taken up in methylene chloride and washed with water, then with hydrochloric acid solution and then with water 162 mg of crude reaction material was obtained.

The material obtained was purified on a column of silica with a pentane/ether (90/10) eluent. An 88 mg fraction was obtained with a yield of 53%.

45% of the cis isomer 9 and 55% of the trans isomer 9 were obtained.

EXAMPLE 9

Partial rearrangement of the C₁₈ ketone (II, A=CH₃, X=a carbon atom)

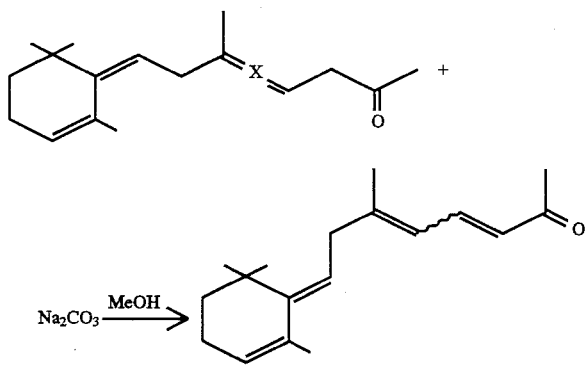

550 mg (2.12×10³ mol) of the product obtained in Example 4 dissolved in 51 ml of methanol, was introduced into a round-bottomed flask. The temperature was maintained at about 20° C. 44.4 mg of NaHCO₃ were added. The mixture was maintained for 1 hour 30 minutes at 20° C.

The methanol was concentrated under vacuum. The residue was taken up in ether, washed with water until neutral and then dried over MgSO₄.

517 mg of crude reaction mass was obtained.

Separation was performed on a column of silica, eluting with a pentane/Et₂O (85/15) mixture.

342 mg of a mixture composed of the following isomers was recovered:

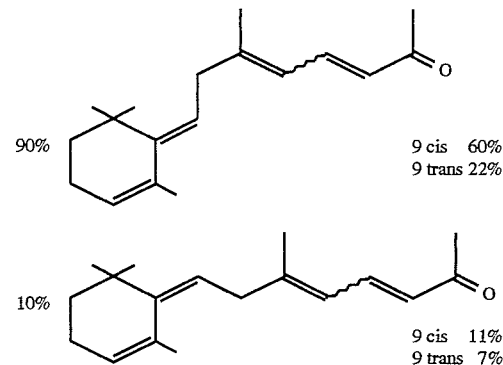

The yield was 62%.

What is claimed:

1. A compound corresponding to the formula (III):

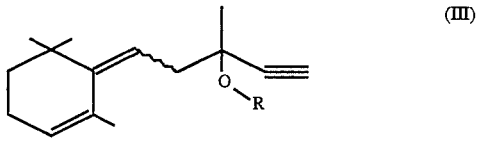

in which R represents a hydrogen atom, an alkyl group having 1 to 10 carbon atoms, an alkenyl group having 2 to 10 carbon atoms, an alkylcarbonyl, alkenylcarbonyl, alkoxyalkyl or alkoxyalkenyl group in which the alkyl groups have 1 to 10 carbon atoms and the alkenyl groups have 2 to 10 carbon atoms, each of said groups being linear or branched and each being substituted or unsubstituted.

2. A compound according to claim 1 wherein R represents hydrogen.

* * * * *